United States Patent [19]

Hagen

[11] 4,059,169

[45] Nov. 22, 1977

[54] MONITOR FOR BIOLOGICAL VOLUME CHANGES

[76] Inventor: Winston H. Hagen, 36 Husted Lane, Greenwich, Conn. 06830

[21] Appl. No.: 656,399

[22] Filed: Feb. 9, 1976

[51] Int. Cl.² .................................................. A61B 5/02
[52] U.S. Cl. ............................. 128/2.05 V; 128/2.1 Z; 73/194 E; 328/127
[58] Field of Search ............... 128/2.05 V, 2.05 F, 128/2.05 R, 2.1 Z, 2.1 P; 328/127; 73/194 E; 235/150.51

[56] References Cited

U.S. PATENT DOCUMENTS

| 2,661,734 | 12/1953 | Holzer et al. | 128/2.1 Z |
|---|---|---|---|
| 3,340,867 | 9/1967 | Kubicek et al. | 128/2.05 V |
| 3,374,362 | 3/1968 | Miller | 328/127 X |
| 3,433,936 | 3/1969 | Blanke | 328/127 X |
| 3,488,597 | 1/1970 | Schlein | 328/127 X |
| 3,558,867 | 1/1971 | Pahl, Jr. | 328/127 X |
| 3,623,473 | 11/1971 | Andersen | 128/2.05 V X |
| 3,835,840 | 9/1974 | Mount | 128/2.05 V |
| 3,874,368 | 4/1975 | Asrican | 128/2.05 V X |
| 3,896,373 | 7/1975 | Zelby | 128/2.05 V |

OTHER PUBLICATIONS

Peiss et al., "An Integrating Drop-Flowmeter . . . Recording", IRE Trans. on Med. Elec., Dec., 1959, pp. 234–237.
Moffitt, "A Versatile . . . Plethysmograph", ISA, 1972, vol. 9, pp. 15–20.

Primary Examiner—Robert W. Michell
Assistant Examiner—Lee S. Cohen
Attorney, Agent, or Firm—Alfred E. Miller

[57] ABSTRACT

A monitor for biological volume changes such as fluid content changes includes a source of constant current oscillations for application to the biological volume, and a receiver adapted to be coupled to the biological volume for producing a direct voltage having an amplitude corresponding to the impedance of the biological volume. A display device provides a display responsive to the D.C. voltage. A filter is provided for filtering the voltage, the filter having a time constant up to 15 seconds.

12 Claims, 2 Drawing Figures

MONITOR FOR BIOLOGICAL VOLUME CHANGES

BACKGROUND OF THE INVENTION

The importance of determining biological volume changes such as changes in fluid content of biological volumes has been recognized and reported, for example, by M. Pomerantz et al, in "Annals of Surgery," Vol. 171, No. 5, May 1970, at pages 686-691; by I. R. Berman et al, in "Archives of Surgery," Vol. 102, Jan. 1971, at pages 61-64; by J. N. Van deWater et al, in "Chest," Vol. 64 of Nov. 1973, at pages 597-603; and by R. V. Luepker et al in "American Heart Journal," Vol. 85, No. 1, Jan. 1973, at pages 83-93.

It has further been found, as reported in these publications, that the electrical impedance of biological volumes is correlated closely with the fluid content of the biological volumes.

In a conventional technique for measuring fluid volume, for example, intrathoracic fluid volume, the trans-thoracic electrical impedance is measured by connecting a constant current oscillator, of a frequeny of, for example, 100 kHz, between the neck and the lower abdomen of a patient. Voltage pickup electrodes are connected to the base of the neck of the patient and to a region slightly below the xiphisternal joint of the patient. The voltage at the pickup electrodes is applied through a receiver including an amplifier and a detector. The detected voltage output of the receiver is applied to a display device, such as a strip chart recorder or a digital indicator. The display device thus indicates the eletrical impedance between the pickup electrodes.

The equipment which may be employed for this type of measurement is disclosed, for example, in U.S. Pat. No. 3,340,867 to Kubicek, and U.S. Pat. No. 3,874,368 to Asrican.

The importance of measuring the trans-thoracic electrical impedance is apparent from the reports, which indicate that this technique may be applied to detect the early occurrence of fluid—intra or extra pulmonary—which is not easily found by auscultation or x-ray techniques. Thus, the above Pomerantz et al publication reports changes in the electrical impedance as much as 45 minutes prior to detectable alterations in central venous pressure, pulmonary compliance, arterial pressure, or changes in blood gases. The Van deWater publication further reports detectable drops in impedance resulting from over-hydration that were too subtle to be appreciated clinically or by x-ray examination.

In measurement of the electrical impedance of biological volumes by the above technique, intrathoracic gas and biological fluids are the main variable components. As a result, the impedance measured varies cyclically with the cardiac output, as well as with respiration. In addition, variation is noted due to movement of the subject. Such cyclic variation is shown, for example, in the above-mentioned U.S. Pat. No. 3,874,368. In view of this cyclic variation of the electrical impedance, various techniques have been employed in the past for determining overall changes in the electrical impedance that could be correlated with variation in the tissue fluid content. For example, as reported in the above publication of Van deWater et al, only the lowest readings are recorded, which occur at the end of expiration and correspond to the functional residual capacity level, so that respiratory variations which vary from 1.0 to 2.0 ohms with a vital capacity maneuver are avoided. In general, the observations of variation in electrical impedance for this purpose have required "eye-balling" of the recorder chart and manual averaging and plotting techniques. It was not possible in prior equipment to ascertain edema with the digital indicator, nor was it possible to obtain an automatic printout of values suitable for reliable indication of variation in tissue fluid content.

The present invention is therefore directed to the provision of means for readily indicating changes as fluid content changes of biological volumes, whereby the observer is not required to guess or estimate the values, nor to employ only certain portions of a cyclically varying electrical impedance measurements for ascertaining fluid changes.

Briefly stated, in accordance with the invention, a non-invasive monitor, such as a fluid monitor, is provided for overcoming the above problems, wherein means are provided for electronically averaging detected signals corresponding to the instantaneous electrical impedance of the biological volume under investigation. The time constant of the averaging circuit is preferably in the range of 2 seconds to 15 minutes, so that variations due to cardiac output, respiration and movement do not interfere with the measurement. As a consequence, the recorder provides a recording which is related directly to the fluid content of the tissue under investigation without the necessity for mental averaging or plotting, whereby inexperienced clinical personnel may be able to readily interpret the recording. In addition, due to the averaging of the signals, it is possible to employ a digital readout corresponding to fluid volume.

In a particularly advantageous environment of the invention means are provided for varying the time constant of the circuit so that it may be adapted to any desired conditions and in order to enable use of the equipment for other purposes, the variation of time constant may fall within the range of about 0 to 15 seconds.

In a simple environment of the invention, the time constant may be controlled as a function of the capacity of a capacitor in an amplifier in the circuit, whereby variation of the time constant of the circuit may be varied by varying the capacity of the capacitor.

The term "time constant" is employed in its specific sense, as a measure of a transient condition in a circuit having a resistance and a reactance. While a circuit in accordance with the invention may employ a resistance and a capacitance in the time constant circuit, the term is employed herein in its more general sense as a matter of the time that it takes a varying value to obtain 63% of its ultimate value once starting at an initial value, assuming no variation in the conditions causing the change of the value.

In order that the invention will be more clearly understood, it will now be disclosed in greater detail with reference to the accompanying drawings, wherein:

FIG. 1 is a simplified illustration of the use of known equipment in the measure of electrical impedance of biological volume; and FIG. 2 is a simplified illustration of a circuit in accordance with the present invention, for non-invasively measuring fluid variation in biological volumes.

DESCRIPTION OF THE PREFERRED EMBODIMENT

Figure 1:
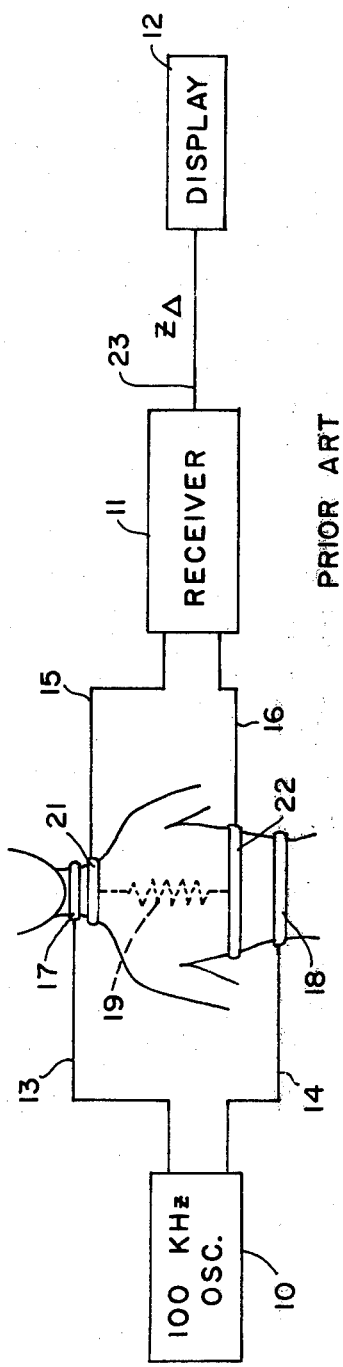

Referring now to the drawings, and more particular to FIG. 1 which is a known system for determining the electrical impedance of biological volumes, and are generally comprised of an oscillator 10, a receiver 11, and a suitable display device 12. The oscillator 10, which may include, for example a 100 kHz oscillator adapted to provide constant current output as a pair of output conductors 13, 14, while the receiver 11 has a pair of input conductors 15, 16. In the measurement of trans-thoracic impedance, the output line 13 of the oscillator is connected to an electrode 17 at the upper neck of the subject, and the output line 14 of the oscillator is connected to an electrode 18 at the lower abdomen. This results in a constant current flowing through the trans-thoracic impedance of the subject, as indicated by the reference numeral 19.

The receiver line 15 is connected to an electrode 21 at the base of the neck, and the receiver line 16 is connected to an electrode slightly below the xisphisternal joint of the subject. As a result of the current flowing through the impedance 19, a voltage is developed between the lines 15 and 16, the amplitude of the voltage being a function of the impedance 19. This voltage is amplified and detected in the receiver, for example, to give an analog voltage on the output line 23 corresponding to the electrical impedance $Z_o$ of the subject between the electrodes 21 and 22. This analog voltage is applied to a suitable display device 12, such as a strip chart recorder, so that the electrical impedance $Z_o$ and variations thereof are observable.

As previously discussed, the indication given on the display device, is such an arrangement according to the prior art varying cyclically with the cardiac output, and the respiration of the subject, and variations are also caused by motion of the subject.

While the average value of the indication on the display device is correlated with the fluid volume in the thoracic region of the subject, it is difficult for an observer to ascertain this volume from such a cyclically varying indication, and hence techniques such as mental averaging, plotting and the like have always been resorted to in the past for employing such equipment in the determination of the fluid content of the biological volume.

Figure 2:
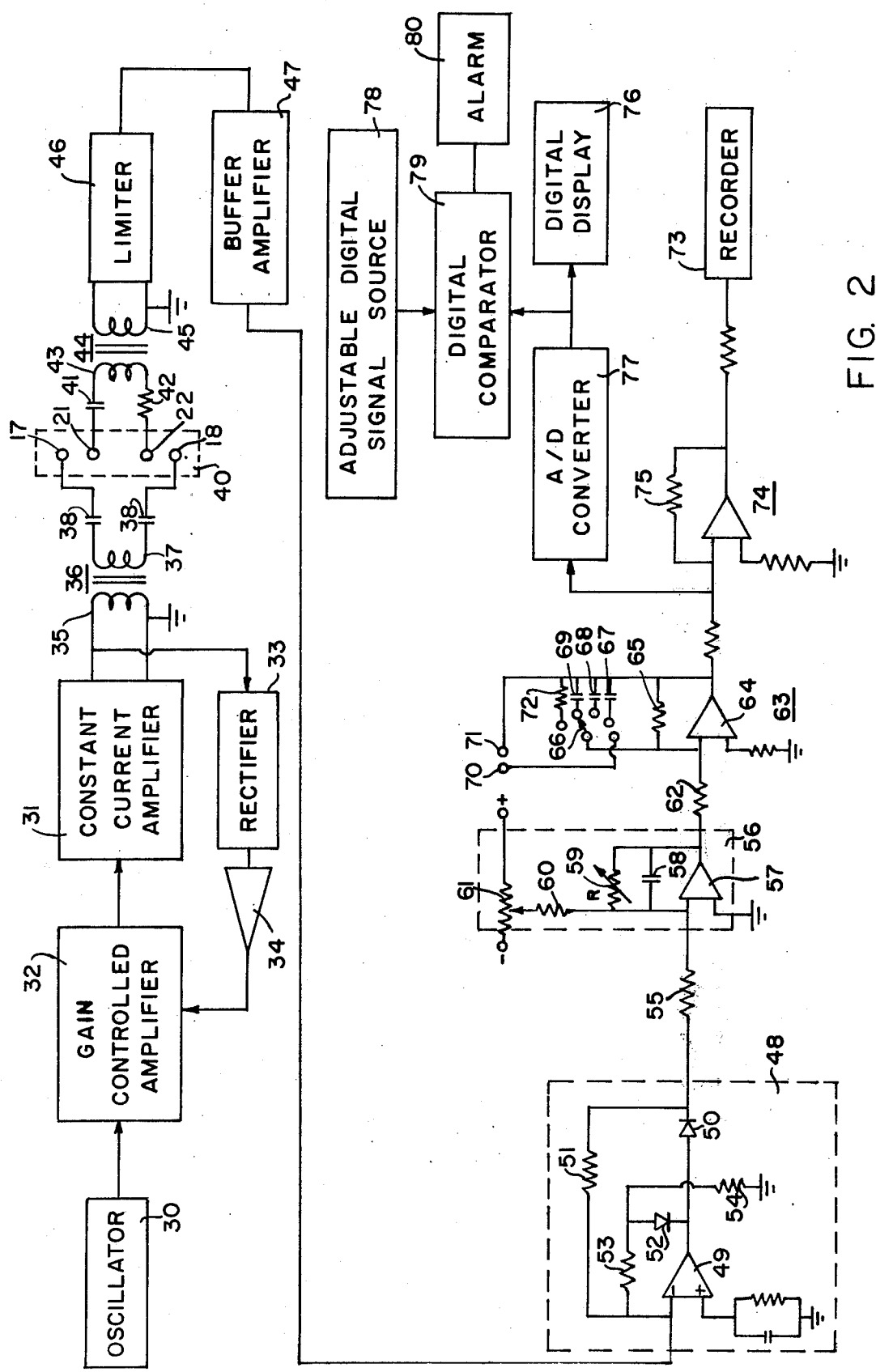

Referring now to FIG. 2, therein is illustrated a block diagram of a non-invasive fluid monitor in accordance with the invention. The transmitter section of the fluid monitor is comprised of an oscillator 30, which may, for example, be a 100 kHz oscillator. The output of the oscillator 30 is applied to a constant current amplifier 31 by way of a gain controlled amplifier 32. In order to maintain the output of the amplifier 31 constant, the output of this amplifier is rectified by a rectifier 33 and applied by way of an amplifier 34 to the gain control terminal of the gain controlled amplifier 32. As a result, the oscillations applied to the primary winding 35 of isolation transformer 36 are constant. The secondary winding 37 of the transformer 36 are applied by way of isolation capacitors 38 to the electrodes 17 and 18. These electrodes are adapted to be applied to the biovolume as above discussed. The oscillations applied to the biovolume are in the form of substantially pure sine wave oscillations of the centrally constant current of for example about 3 millliamps. As a result, it is apparent that the voltage developed across the resistance of the biovolume, between the electrodes 21 and 22, will be proportional to the resistance of the biovolume 40.

The electrodes 21 and 22 are applied by way of a capacitor 41 and resistor 42, respectively, to the primary end 43 of an isolation transformer 44. The secondary winding 45 of this transformer is applied to a limiter 46, and thence to a buffer amplifier 47, for maintaining the necessarily high input impedance of for example greater than 50,000 ohms of the receiver.

The output of the buffer amplifier 47 is applied to a high frequency "ideal diode" detector 48. This detector may be comprised of an operational amplifier 49, such as an RCA CA3100A amplifier. The output of the amplifier is returned to the input inverting terminal by way of a diode 50 and resistor 51, as well as by a diode 52 of reversed polarity and a resistor 53, with the junction of the diode 52 and resistor 53 being connected to reference ground by a resistor 54.

The output of the ideal diode detector 48, at the junction of the diode 50 and the resistor 51, is applied by way of a resistor 55 to an amplifier filter 56. This amplifier filter may be comprised of an amplifier 57, such as a Raytheon 4136, with a feedback path including a parallel capacitor 58 and variable resistor 59 for calibrating the gain of the system. The negating terminal of the amplifier is connected by way of a resistor 60 to the arm of a potentiometer 61, the potentiometer being connected between the negative and positive supply terminals for calibrating the system.

In accordance with the invention, the output of the amplifier filter 56 is applied by way of a resistor 62 to a low pass filter 63. The filter 63 may be comprised of an operational amplifier 64 such as a Raytheon 4136 having a resistor 65 of, for example, 100 kilohms connected inthe feedback path. The time constant of the filter 63 is controlled by providing a capacitor in parallel with the resistor 65, for example, a switch 66 may be provided to connect any of capacitors 67, 68, or 69 in parallel with the resistor 65, or any capacitor may alternatively be connected between the externally available terminals 70, 71. As a result, the filter 63 will have a time constant dependent upon the resistor 65 and the capacitor connected in parallel therewith. Since, during calibration of the system, it is undesirable to have a time constant in the low pass filter, the switch 66 may have a position in which it connects a calibration resistor 72 between the input and output of the amplifier. This resistor may, for example, be 25.5 ohms.

In one form of display of the fluid volume of the biovolume 40, the output of the filter 63 is applied to a recorder 73, such as a strip chart recorder by way of an amplifier 74. This amplifier may comprise an operational amplifier with a suitable feedback resistor 75 for expanding the scale of the recorder, for example by a factor of 10.

In addition, the output of the filter may be employed to activate a digital display 76, the output of the filter 63 being connected to an analog to digital converter 77 of conventional nature for producing digital signals for operations of the display 76.

The system in accordance with the invention also enables a giving of an alarm when the impedance being measured exceeds a predicted value. For this purpose, an adjustable digital signal source 78 is provided. The source 78, which is preferably manually adjustable, provides output digital signals in accordance with its setting. The outputs of the analog to digital converter 77 and the digital signal source 78 are applied to a digital comparator 79 of conventional nature, and the output of the digital comparator 79 is connected to actuate a suitable audible or visual alarm device 80.

For operation of the system as a non-invasive fluid monitor, the low pass filter 63 should have a time constant between 2 seconds and 15 minutes, determined in accordance with the capacitor connected in the feedback circuit. This can, of course, be effected by the use of switch to capacitors 67, 68, or 69 in the system itself, or by the use of a capacitor connected between the external terminals 70, 71. If the time constant is less than about 2 seconds, the effects of breathing and movement of the patient may interfere with the indications, while time constants up to about 15 minutes are desirable, since such longer time constants enable measurements to be taken, for example, on an hourly basis, when a patient is permitted to move around.

When the system is to be calibrated, by connecting the resistor 72 in the feedback circuit, it is preferred that no capacitor be connected in the feedback circuit, since such a capacitor would only unnecessarily increase the time necessary to calibrate the instrument.

It is, of course, apparent that the instrument may be employed for other purposes, such as a plethysmograph, by removal of all capacitors, so that the time constant of the low pass filter is effectively zero (real time). Thus, for a wide range of applications of the instrument, including use thereof as a fluid monitor, provision may be made for adjusting the time constant between effectively zero seconds and about 15 minutes. In one example of the invention, a capacitor of 15 microfarads was employed in the feedback circuit to provide a time constant of about 10 seconds.

Due to the use of the time constant, the instrument in accordance with the invention provides a direct reading of impedance $Z_o$ of the biovolume so that it is not necessary for the user of the instrument to estimate this impedance or employ the other previously discussed time consuming techniques. The strip chart recorder may thus be employed to continuously monitor the impedance providing a clearly readable measurement of the impedance. In addition, due to the use of the time constant, the system in accordance with the invention can employ a digital display, which was not feasible in accordance with the previously known techniques for determining fluid content of a biovolume. In addition, the instrument in accordance with the invention, as discussed above, may employ an alarm circuit so that a visual or audible signal is given when the impedance falls, for example below a predetermined value. The instrument in accordance with the invention thereby is readily adaptable to clinical use, requiring a minimum of training on the part of the operator, and not dependent upon estimations. While the invention has been disclosed and described with reference to a single embodiment it will be apparent that variations and modifications may be made therein and it is therefore intended in the following claims to cover each such variation and modification as falls within the true spirit and scope of the invention.

What is claimed is:

1. In a monitor for measuring biological volume changes having means for applying constant A.C. current in a biological volume of a subject, receiver means including means for sensing voltage across said biological volume resulting from said A.C. current, means for rectifying said sensed voltage, display means, and means for applying said rectified voltage to said diplay means to display a value representing the electrical impedance of said biological volume, the improvement wherein said means for applying said rectified voltage to said display means comprises filter means for inhibiting variations of said displayed value due to respiration and movement of said subject, said filter means having a time constant between 2 seconds and 15 minutes, said filter means comprising substantially the only signal modifying means between said rectifying means and display means.

2. The monitor of claim 1 wherein said filter means has a time constant of about 8 seconds.

3. The monitor of claim 1 further comprising means for calibrating said monitor, and means responsive to the calibration of said monitor for reducing the time constant of said filter means.

4. The monitor of claim 1 wherein said filter means comprises an operational amplifier having a feedback path, a capacitor, and means for connecting said capacitor in said feedback path whereby said capacitor determines said time constant.

5. The monitor of claim 4 further comprising a calibration resistor, said means for connecting said capacitor comprising means for selectively connecting said capacitor and resistor in said feedback path, whereby the time constant of said filter means is reduced when said calibration resistor is connected in said feedback path for calibration of said monitor.

6. The monitor of claim 1 wherein said display means comprises a strip chart recorder.

7. The monitor of claim 1 wherein said display means is a digital indicator, and further comprising analog to digital converter means connected between said receiver means and display means.

8. The monitor of claim 1 further comprising an alarm means, a source of a digital signal corresponding to a determined electrical impedance, analog to digital converter means connected to the output of said receiver means, means for comparing the outputs of said converter means and said source, and means for applying the output of said comparing means to said alarm means.

9. In a non-invasive fluid monitor for measuring bioelectric impedance having means for applying constant A.C. current to a biological volume of a subject, receiver means including means for sensing voltage across said biological volume resulting from said A.C. current, means for rectifying said sensed voltage, display means, and means for applying said rectified voltage to said display means whereby said display means indicates a value representing the electrical impedance of said biological volume, the improvement wherein said means for applying said rectified voltage to said display means comprises filter means, and means for varying the time constant of said filter means from about 0 to 15 minutes, said filter means comprising substantially the only signal modifying means in said means for applying said rectified voltage to said display means.

10. The fluid monitor of claim 9 wherein said filter means comprises an operational amplifier having a feedback path, said means for varying said time constant comprising capacitor means, means for connecting said capacitor means in said feedback path for determining the time constant of said filter means, and means for varying the capacity of said capacitor means.

11. The fluid monitor of claim 10 further comprising a calibration resistor, and means for selectively interconnecting said calibration resistor and capacitor means in said feedback path, whereby said time constant is reduced when said calibration resistor is connected in said feedback path.

12. A non-invasive fluid monitor comprising an impedance plethysmograph means for producing a voltage corresponding to electrical impedance of a biological volume, filter means having a time constant between 2 seconds and 15 minutes for filtering said voltage, display means, and means applying the output of said filter means to said display means, whereby the display on said display means corresponds to the fluid content of said biological volume.

* * * * *